United States Patent [19]

Saarela et al.

[11] Patent Number: 5,298,077
[45] Date of Patent: Mar. 29, 1994

[54] CLEANING DEVICE FOR DENTAL APPLIANCE AND METHOD

[76] Inventors: Wayne E. Saarela; Virginia M. Saarela, both of 32316 Pine, Grayslake, Ill. 60030

[21] Appl. No.: 937,958

[22] Filed: Aug. 28, 1992

[51] Int. Cl.⁵ ............................................. A46B 15/00
[52] U.S. Cl. .................................... 134/6; 15/21.1; 15/104.92; 15/104.94; 15/160; 15/167.2
[58] Field of Search ............... 15/21.1, 160, 104.92, 15/104.94, 167.1, 167.2; 134/6

[56] References Cited

U.S. PATENT DOCUMENTS

| | | | |
|---|---|---|---|
| 1,845,315 | 2/1932 | Meikle | 15/104.92 |
| 2,102,643 | 12/1937 | Pellegrini | 15/104.001 |
| 2,122,583 | 7/1938 | Parizot | 141/1 |
| 2,444,294 | 6/1948 | Jones | 206/1 |
| 2,565,899 | 8/1951 | Wilcox | 134/161 |
| 2,568,838 | 9/1951 | Wilcox | 134/154 |
| 2,769,193 | 11/1956 | Jackson | 15/210.1 |
| 2,973,767 | 3/1961 | Cohen | 132/84 |
| 3,135,987 | 6/1964 | Huch | 15/104.92 |
| 3,230,572 | 1/1966 | Leonard | 15/167.1 |

FOREIGN PATENT DOCUMENTS 571856  1/1976  Switzerland ............ 15/21.1

Primary Examiner—Edward L. Roberts
Attorney, Agent, or Firm—Charles F. Meroni, Jr.

[57] ABSTRACT

The device for cleaning a dental appliance includes a round casing made of two pieces. The appliance and a cleaning paste are placed within the casing and bristle tufts within the casing are caused to scrub the appliance by turning the casing pieces opposite to one another. After scrubbing, the device with the appliance therein is placed in a path of running water, with the water running through the device through a plurality of openings provided in a peripheral wall thereof. The appliance may then be removed or allowed to dry within the device.

18 Claims, 2 Drawing Sheets

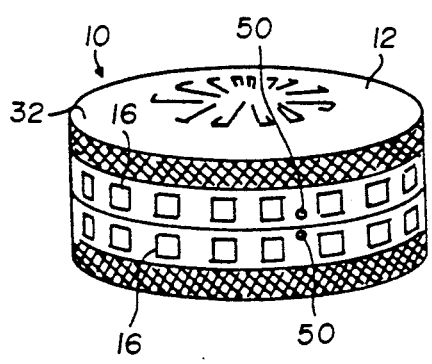
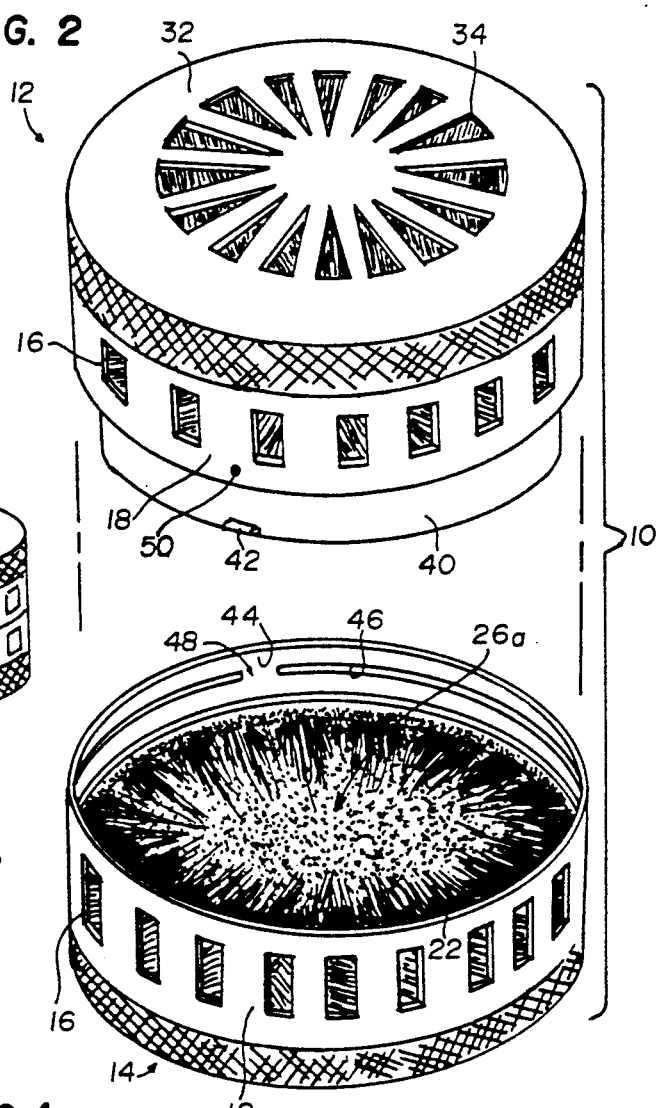
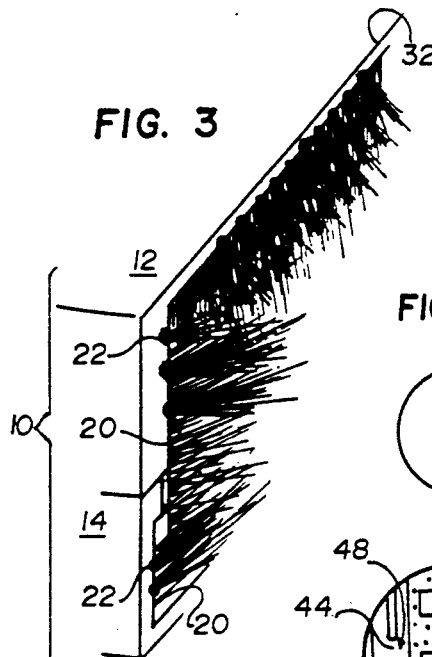
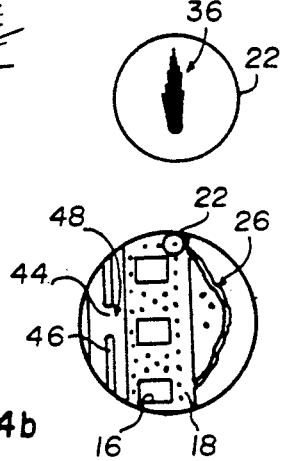
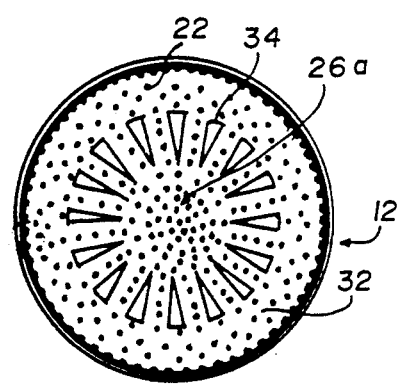

CLEANING DEVICE FOR DENTAL APPLIANCE AND METHOD

BACKGROUND OF THE INVENTION

1. Field of the Invention

The present invention relates to a cleaning device for a dental appliance, such as a denture. More particularly, the cleaning device incorporates structure therein for scrubbing the appliance clean rather than merely shaking the appliance clean in a solution.

2. Description of the Prior Art

Heretofore various devices for use in cleaning a dental appliance by shaking same in a cleaning solution have been proposed.

Various embodiments of such devices are disclosed in the following U.S. patents:

| U.S. Pat. No. | Patentee |
| --- | --- |
| 2,102,643 | Pellegrini |
| 2,122,583 | Parizot |
| 2,565,899 | Wilcox |
| 2,568,838 | Wilcox |

All of these patents basically show two cup halves which cooperate to receive a dental appliance and a cleaning solution therein, with the cup member formed being manually shaken, causing the solution to disperse within the container to clean the appliance.

As will be described in greater detail hereinafter, no device has been proposed for use in scrubbing the dental appliance clean to remove stubborn particles that may remain trapped within crevices between the teeth, even after solution cleansing.

Summary of the Invention

According to the invention there is provided a device for cleaning a dental appliance by producing a scrubbing action thereagainst, the device comprising a hollow, circular case formed of two coacting elements comprising a top half and a bottom half, each half including a planar circular wall and an upstanding peripheral wall, each peripheral wall having a plurality of spaced apart slots therein and each wall further having bristle tufts extending inwardly therefrom, from an interior surface thereof, tufts which rise from the circular wall being shorter than the peripheral bristle tufts to create a small cavity therebetween within which a dental appliance may be accommodated, and the halves being oppositely rotatable relative to one another.

Further according to the invention there is provided a method for using the device comprising the steps of: separating the casing pieces; placing a dental appliance within one of the pieces and a dental cleaning paste in the other piece; engaging the pieces together; allowing a small amount of water to enter the casing through the plurality of openings; rotating the casing pieces oppositely to one another in alternating directions to cause a scrubbing of bristles against the dental appliance; placing the device beneath running water to rinse the interior of the device and the appliance therein via the openings in the peripheral walls; and allowing the device to air dry.

Still further according to the invention there is provided a device for cleaning a dental appliance by producing a scrubbing action thereagainst, the device comprising a hollow, circular case formed of two coacting elements comprising a top half and a bottom half, each half including a planar circular wall and an upstanding peripheral wall, each upstanding peripheral wall having bristle tufts extending inwardly therefrom, from an interior surface thereof, tufts also rising from the circular wall and being oriented to provide a small cavity therebetween within which a dental appliance may be accommodated, and the halves being oppositely rotatable relative to one another, the top half round planar wall includes a radial array of slots therein for passing water to assist in the scrubbing action.

BRIEF DESCRIPTION OF THE DRAWINGS

FIG. 1 is a perspective view of the cleaning device of the present invention.

FIG. 2 is an exploded perspective view showing the halves of the device separated.

FIG. 3 is a sectional view through an edge area of the device of FIG. 1.

FIGS. 4a–4c show a bottom plan view of a top half of the device of FIG. 2 with an edge portion thereof shown enlarged and with a detail of a bristle thereof.

DESCRIPTION OF THE PREFERRED EMBODIMENT

Figure 5:
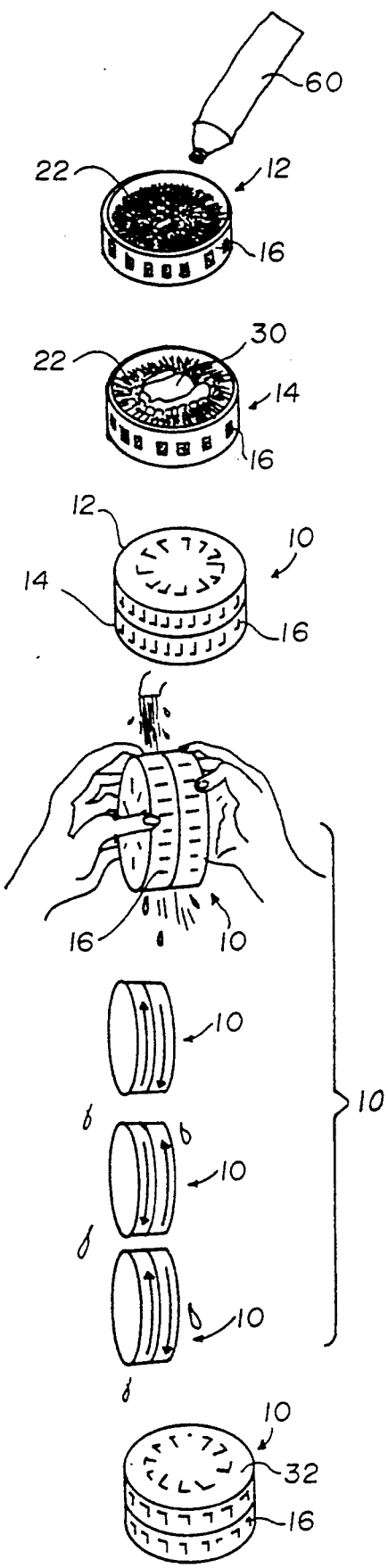
FIG. 5 shows the method of use of the device of the present invention.

Referring now to the drawings in greater detail, there is illustrated therein the cleaning device for a dental appliance of the present invention generally referred to by the reference numeral 10.

As shown, the device 10 comprises a hollow circular case 10 formed from two coacting elements, a top half 12 and a bottom half 14 which engage one another to form a sealed case 10.

Openings 16 are provided within a peripheral wall 18 of each half 12 and 14 and extending radially inwardly from an interior surface 20 of each peripheral wall 18 is a plurality of multistrand bristle tufts 22, the tufts 22 being seated between the openings 16.

As shown in FIG. 3, when the halves 12 and 14 are engaged together, an interior 26 formed within the device 10 is substantially filled with bristle tufts 22 extending into the interior 26 from all surfaces of the device 10 and intersecting at points.

A center portion 26a of the interior 26, however, is provided with shorter bristle tufts 22 to allow for a small cavity to exist within which a dental appliance 30 (FIG. 5) may be fitted.

FIGS. 4a–4c provide a plan view of the interior 26 of the upper half 12 and enlarged sectional views therein. As shown, the upper half 12 includes on a circular planar surface 32 thereof a circular array of slots 34. Extending into the interior 26 at positions between the slots 34 are a plurality of bristle tufts 22, the bristles 36 of which are of varied lengths to provide a conical head to each tuft 22.

With respect to engagement of the halves 12 and 14, in a secure manner, it will be noted that one of the halves, here shown to be the top half 12, is provided with a radially inwardly stepped depending neck 40 having a radially outwardly extending tab 42 thereon.

The other half 14 has, on an inner surface 44 of the peripheral wall 18, an inwardly extending peripheral rib 46 which is circumferential. The rib is notched at 48, to allow for passage of the tab 42 into engagement under the rib 46. It will be understood that the halves 12 and 14 are securely engaged so long as the tab 42 remains seated beneath the rib 46, the halves 12 and 14 only being separable or engageable when the tab 42 is aligned with the notch at 48 in the rib 46.

Indicia in the form of an alignment dot 50 are provided on each half 12 and 14 to indicate to the user when the tab 42 and notch at 48 are appropriately aligned.

FIG. 5 shows a method for use of the device 10. As shown, the dental appliance 30, such as the denture 30 is placed within the device half 14, with teeth of the appliance 30 facing downwardly and seating with the bristle tufts 22 therein. The other, top device half 12 is then inverted and an appliance cleaning paste 60 is placed upon the tufts 22.

The halves 12 and 14 are then engaged, with the dental appliance 30 being snugly received with the device 10, and with the cleaning paste 60 pressed by the tufts 22 of the half 12 against an upper surface of the appliance 30.

Next, the device 10 is turned sideways and a small amount of water is allowed to flow into the device 10 through the openings 16 in the peripheral wall 18 of the halves 12 and 14, to turn the cleaning paste 60 into a sudsy solution which may be brushed against all surfaces of the dental appliance 30 by the bristle tufts 22 of the device 10.

The halves 12 and 14 of the device 10 are then oppositely turned back and forth, creating a scrubbing action by the tufts 22 against the appliance 30. Then, the device 10 is again placed under a stream of running water to rinse the cleaning paste 60 away.

The dental appliance 30 may then be removed for use or stored within device 10, as desired.

Further, it will be understood that the device 10 may be provided with only one or the other of the openings 16 in the peripheral walls 18 or the slots 34 on surface or wall 32.

As described above, the device 10 of the present invention and the method of using same provide a number of advantages, some of which have been described above and others of which are inherent in the invention.

It is anticipated that the preferred embodiment will result in the cleaning device being molded from a suitable synthetic plastic material with the bristles or bristle tufts being embedded and secured in the material to hold the bristles or bristle tufts in place.

Also, modifications may be proposed without departing from the teachings herein.

Accordingly, the scope of the invention is only to be limited as necessitated by the accompanying claims.

In the preferred embodiment, we would contemplate that device 10 would have openings and slots 34 in both locations.

I claim:

1. A device for cleaning a dental appliance by producing a scrubbing action thereagainst, the device comprising a hollow, circular case formed of two coacting elements comprising a top half and a bottom half, each half including a planar circular wall and an upstanding peripheral wall, each upstanding peripheral wall having a plurality of spaced apart slots therein and each wall further having bristle tufts extending inwardly therefrom, from an interior surface thereof, tufts which rise from the circular wall being shorter than the peripheral bristle tufts to create a small cavity therebetween within which a dental appliance may be accommodated, and the halves being oppositely rotatable relative to one another.

2. The device of claim 1 wherein said top half round planar wall includes a radial array of slots therein.

3. The device of claim 2 wherein said peripheral inwardly extending bristle tufts intersect with said bristle tufts extending from said planar circular wall on each device half.

4. The device of claim 3 wherein said halves include cooperating engagement means thereon.

5. The device of claim 4 wherein said engagement means on said top half include a depending reduced in diameter neck portion which includes a radially outwardly extending tab thereon.

6. The device of claim 5 wherein said engagement means on said bottom half comprise a circumferential rib on an inner surface of said peripheral wall thereof, said rib having a notch therein through which said tab on said top half can pass.

7. The device of claim 6 wherein indicia are provided on an outer surface of each device half to indicate an alignment between said tab and said rib notch.

8. The device of claim 7 wherein said bristle tufts are comprised of bristles of varied length to create a conical tuft head.

9. A method for using a device for cleaning a dental appliance comprising a round two piece casing having an inner surface from which bristles extend inwardly and having a plurality of openings therein, said method comprising the steps of:
   separating the casing pieces;
   placing a dental appliance within one of the pieces and a dental cleaning paste in the other piece;
   engaging the pieces together;
   allowing a small amount of water to enter the casing through the plurality of openings;
   rotating the casing pieces oppositely to one another in alternating directions to cause a scrubbing of bristles against the dental appliance;
   placing the device beneath running water to rinse the interior of the device and the appliance therein via the openings in the peripheral walls;
   and allowing the device to air dry.

10. A device for cleaning a dental appliance by producing a scrubbing action thereagainst, the device comprising a hollow, circular, case formed of two coacting elements comprising a top half and a bottom half, each half including a planar circular wall and an upstanding peripheral wall, each upstanding peripheral wall having bristle tufts extending inwardly therefrom, from an interior surface thereof, tufts also rising from the circular wall and being oriented to provide a small cavity therebetween within which a dental appliance may be accommodated, and the halves being oppositely rotatable relative to one another, said top half round planar wall includes a radial array of slots therein for passing water to assist in the scrubbing action.

11. The device of claim 10 wherein said peripheral inwardly extending bristle tufts intersect with said bristle tufts extending from said planar circular wall on each device half.

12. The device of claim 11 wherein said halves include cooperating engagement means thereon.

13. The device of claim 12 wherein said engagement means on said top half include a depending reduced in diameter neck portion which includes a radially outwardly extending tab thereon.

14. The device of claim 13 wherein said engagement means on said bottom half comprise a circumferential rib on an inner surface of said peripheral wall thereof, said rib having a notch therein through which said tab on said top half can pass.

15. The device of claim 14 wherein indicia are provided on an outer surface of each device half to indicate an alignment between said tab and said rib notch.

16. The device of claim 15 wherein said bristle tufts are comprised of bristles of varied lengths to create a conical tuft head.

17. The device of claim 10 wherein the bristle tufts have varying lengths, to define the small cavity for receipt of a dental appliance, and means securing the tufts in place interiorly of said halves.

18. The device of claim 17 wherein each upstanding wall has a plurality of spaced apart slots to enable water to be flushed through the small cavity and the bristle tufts to assist in producing the scrubbing action, said upstanding walls having circular radially confronting bearing surfaces which bear against one another as the halves are rotated and with the spaced apart slots allowing water to flush through the radially confronting surfaces for cleansing.

* * * * *